US007848889B2

(12) United States Patent
Xia et al.

(10) Patent No.: US 7,848,889 B2
(45) Date of Patent: Dec. 7, 2010

(54) AUTOMATED ANALYSIS OF MULTIPLEXED PROBE-TARGET INTERACTION PATTERNS: PATTERN MATCHING AND ALLELE IDENTIFICATION

(75) Inventors: Xiongwu Xia, Dayton, NJ (US); Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 1448 days.

(21) Appl. No.: 10/909,638

(22) Filed: Aug. 2, 2004

(65) Prior Publication Data

US 2006/0025930 A1 Feb. 2, 2006

(51) Int. Cl.
*G06F 19/00* (2006.01)
*C12Q 1/68* (2006.01)
(52) U.S. Cl. ............................................. 702/19; 435/6
(58) Field of Classification Search ........................ None
See application file for complete search history.

(56) References Cited

U.S. PATENT DOCUMENTS

| 5,837,832 | A | 11/1998 | Chee et al. |
| 6,287,778 | B1 | 9/2001 | Huang et al. |
| 2001/0049095 | A1 | 12/2001 | Webster |
| 2002/0150909 | A1 | 10/2002 | Stuelpnagel |

FOREIGN PATENT DOCUMENTS

WO WO 2005/045059 A2 5/2005

OTHER PUBLICATIONS

Yeang et al. Molecular classification of multiple tumor types. Bioinformatics vol. 17 Suppl. 1, pp. S316-S322 (2001).*
Duquesnoy HLAMatchmaker: A Molecularly Based Algorithm for Histocompatibility Determination. I. Description of the Algorithm. Human Immunology, vol. 63, pp. 339-352 (2002).*
Mei et al. Genome-wide Detection of Allelic Imbalance Using Human SNPs and High-density DNA Arrays. Genome Research vol. 10, pp. 1126-1137 (2000).*
Gerlach Human Lymphocyte Antigen Molecular Typing. Archives of Patthology & Laboratory Medicine vol. 126, pp. 281-284 (2002).*
Written Opinion of the International Searching Authority.
Pastinene et al. "A system for specific, high-throughput genotyping by allele-specific primer extension on microarrays" Genome Research. vol. 10: 1031-1042 (2000).
Guo Zhen Et. Al: "Oligonucleotide . . . genes" Genome Research, Cold Spring Harbor Laboratory Press,Woodbury, NY, US, vol. 12, No. 3, Mar. 2002, p. 447-457. European Search Report.

* cited by examiner

*Primary Examiner*—John S Brusca
(74) *Attorney, Agent, or Firm*—Womble Carlyle Sandridge & Rice PLLC

(57) ABSTRACT

Disclosed are methods and algorithms (and their implementation) supporting the automated analysis and interactive review and refinement ("redaction") of the analysis within an integrated software environment, for automated allele assignments. The implementation, preferably with a software system and a program referred to as the Automated Allele Assignment ("AAA") program, provides a multiplicity of functionalities including: data management by way of an integrated interface to a portable database to permit visualizing, importing, exporting and creating customizable summary reports; system configuration ("Set-up") including user authorization, training set analysis and probe masking; Pattern Analysis including string matching and probe flipping; and Interactive Redaction combining real-time database computations and "cut-and-paste" editing, generating "warning" statements and supporting annotation. It also includes a thresholding function, a method of setting thresholds, a method of refining thresholds by matching an experimental binary string ("reaction pattern") setting for that probe, probe masking of signals produced by probes which do not contribute significantly to discriminating among alleles.

18 Claims, 12 Drawing Sheets

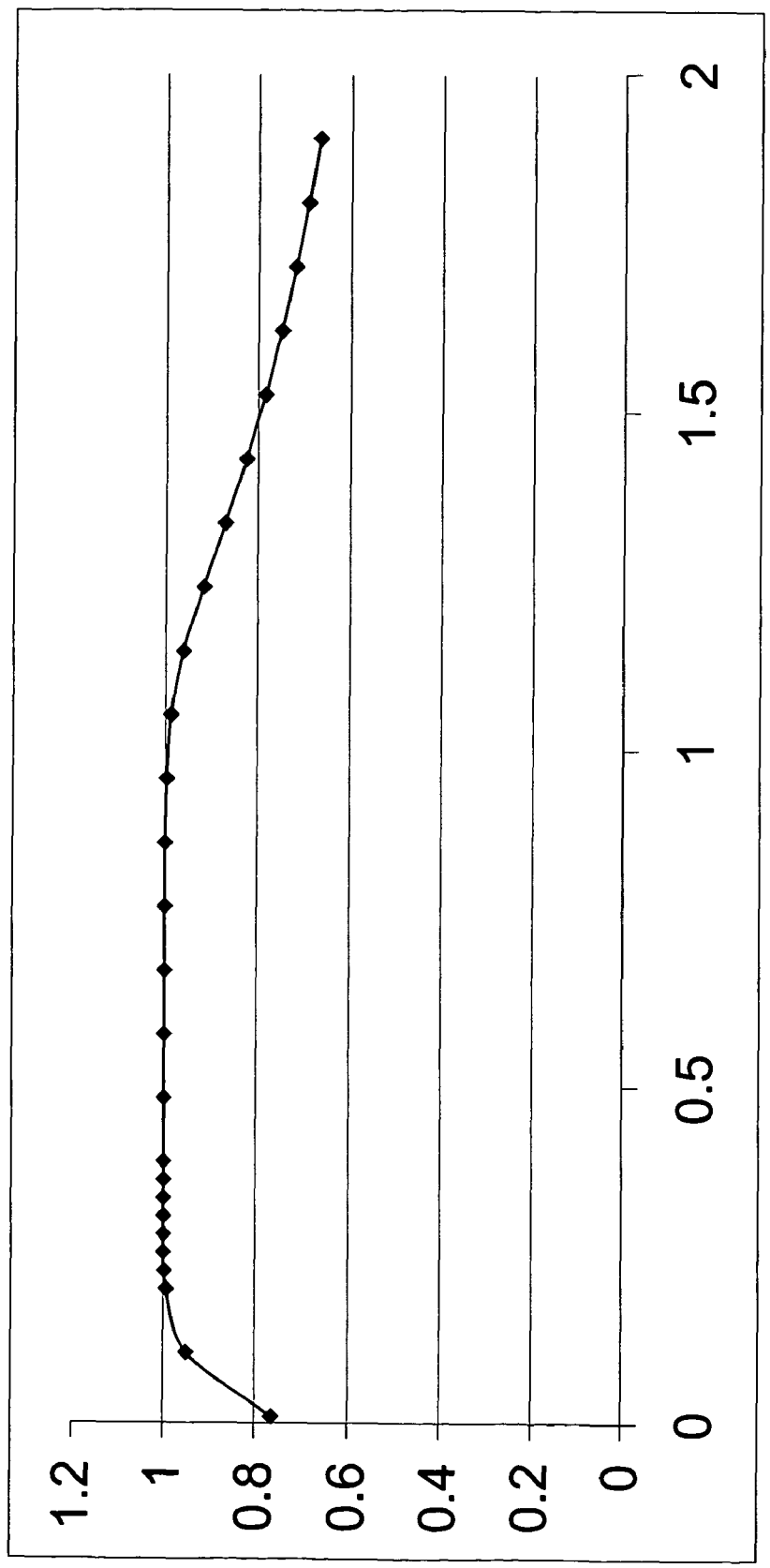
Fig. 1B: Exemplary Empirical Threshold Determination for One Probe

Assignment Adjustment

Assignment Tolerance

HLA-A: 6    HLA-B: 8    HLA-DR: 5

Probe List:

| Probe Name | Required | High Confidence | Low Confidence | Not Used |
|---|---|---|---|---|
| HA114 |  | X |  |  |
| HA114AT |  |  |  | X |
| HA115 |  | X |  |  |
| HA116 |  | X |  |  |
| HA119 |  |  | X |  |
| HA120 |  | X |  |  |
| HA121 |  |  | X |  |
| HA122 |  | X |  |  |
| HA122AT |  |  |  | X |
| HA122B |  |  |  | X |
| HA123 |  | X |  |  |

Fig. 1C: System Settings

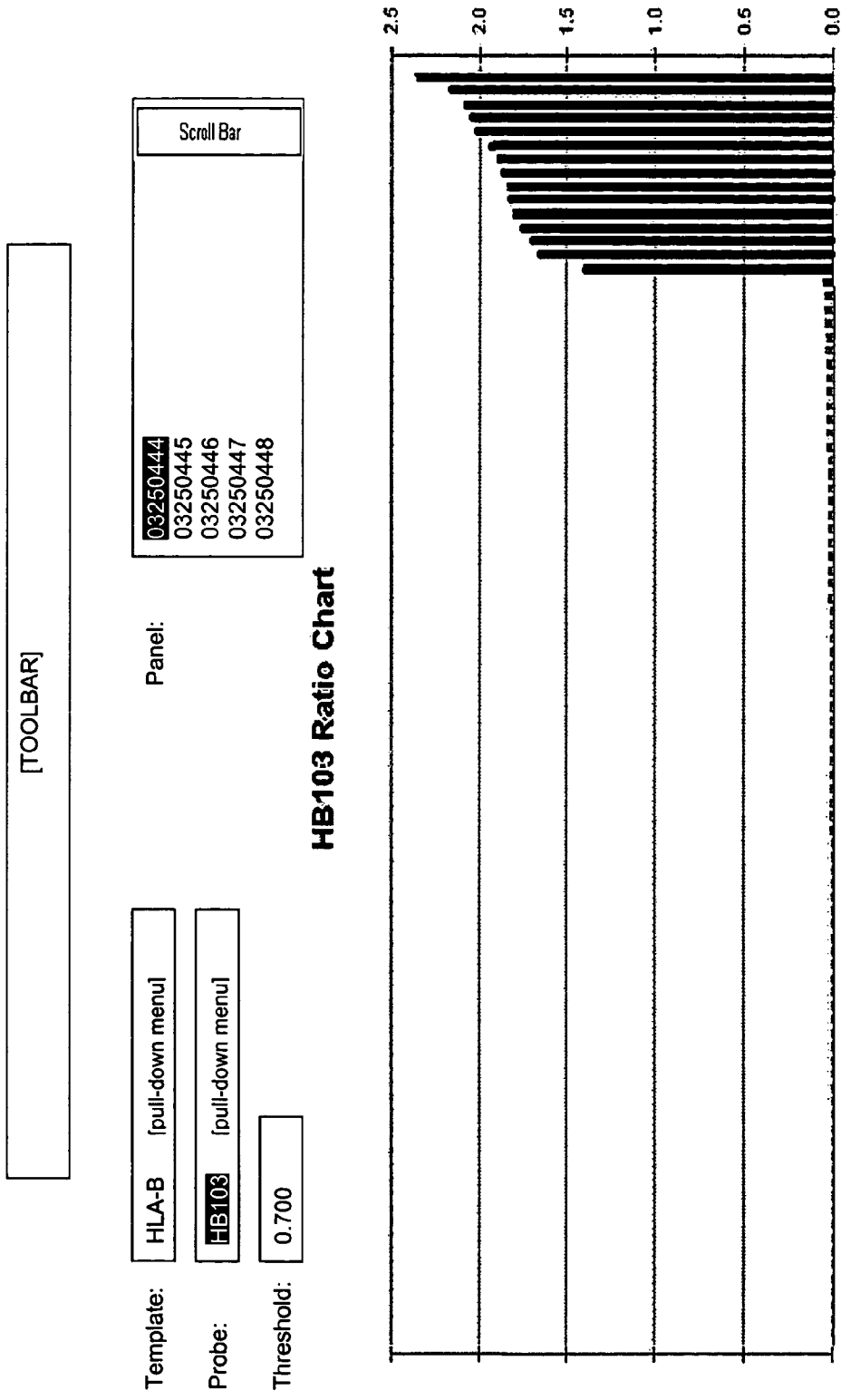
FIG. 2A HB103 Probe Ratio Profile

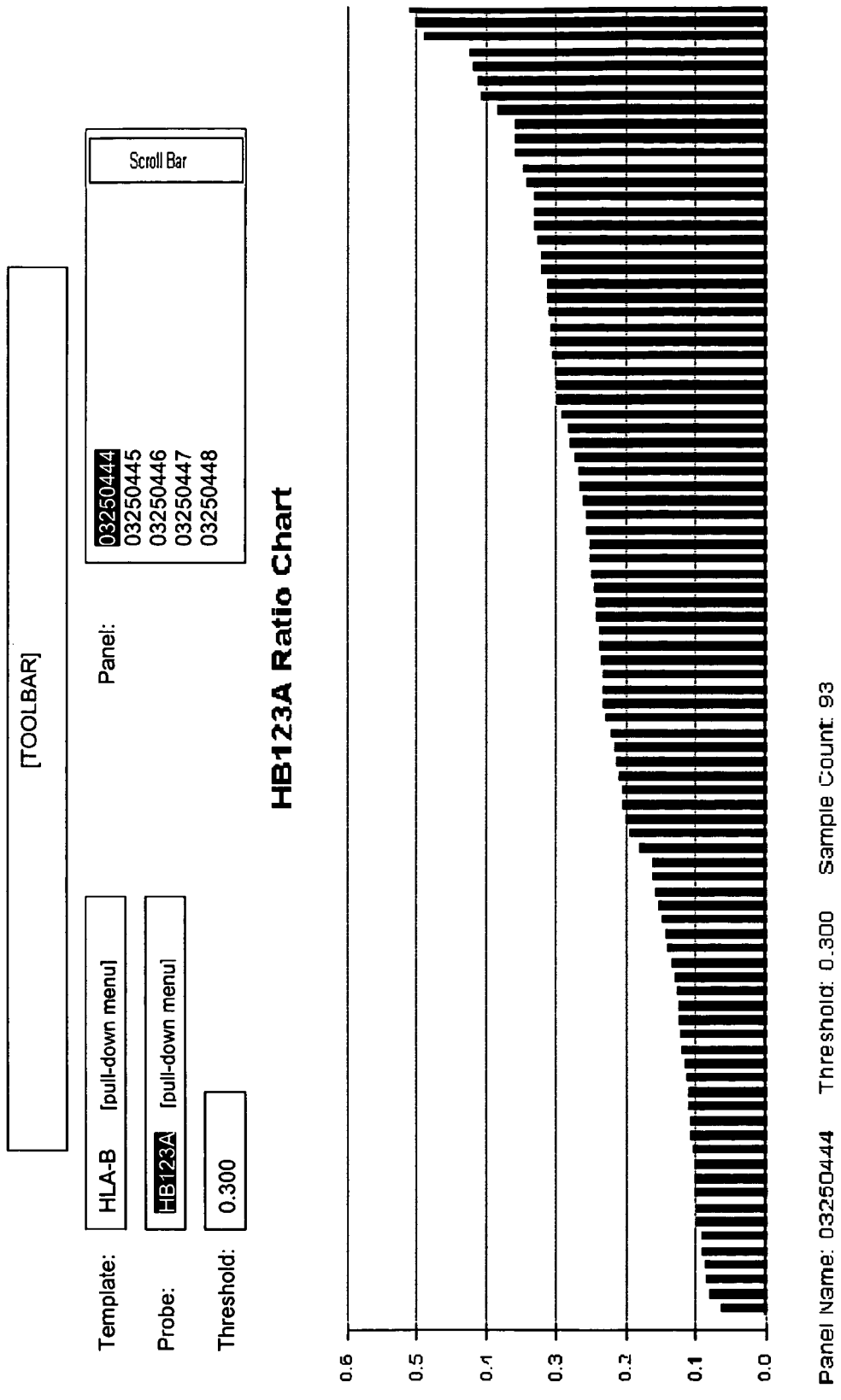
FIG. 2B HB123A Probe Ratio Profile

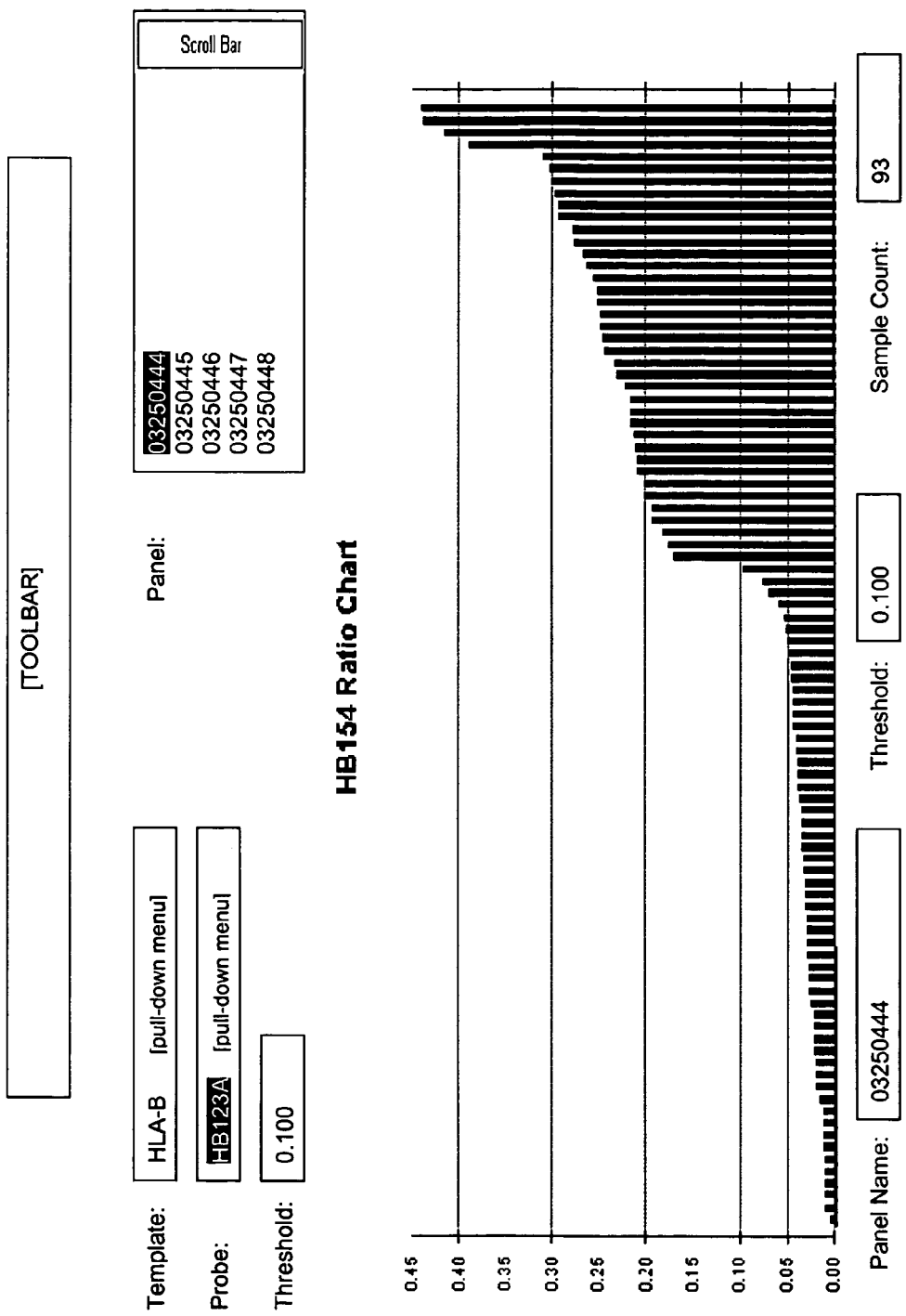
FIG. 2C HB154 Probe Ratio Profile

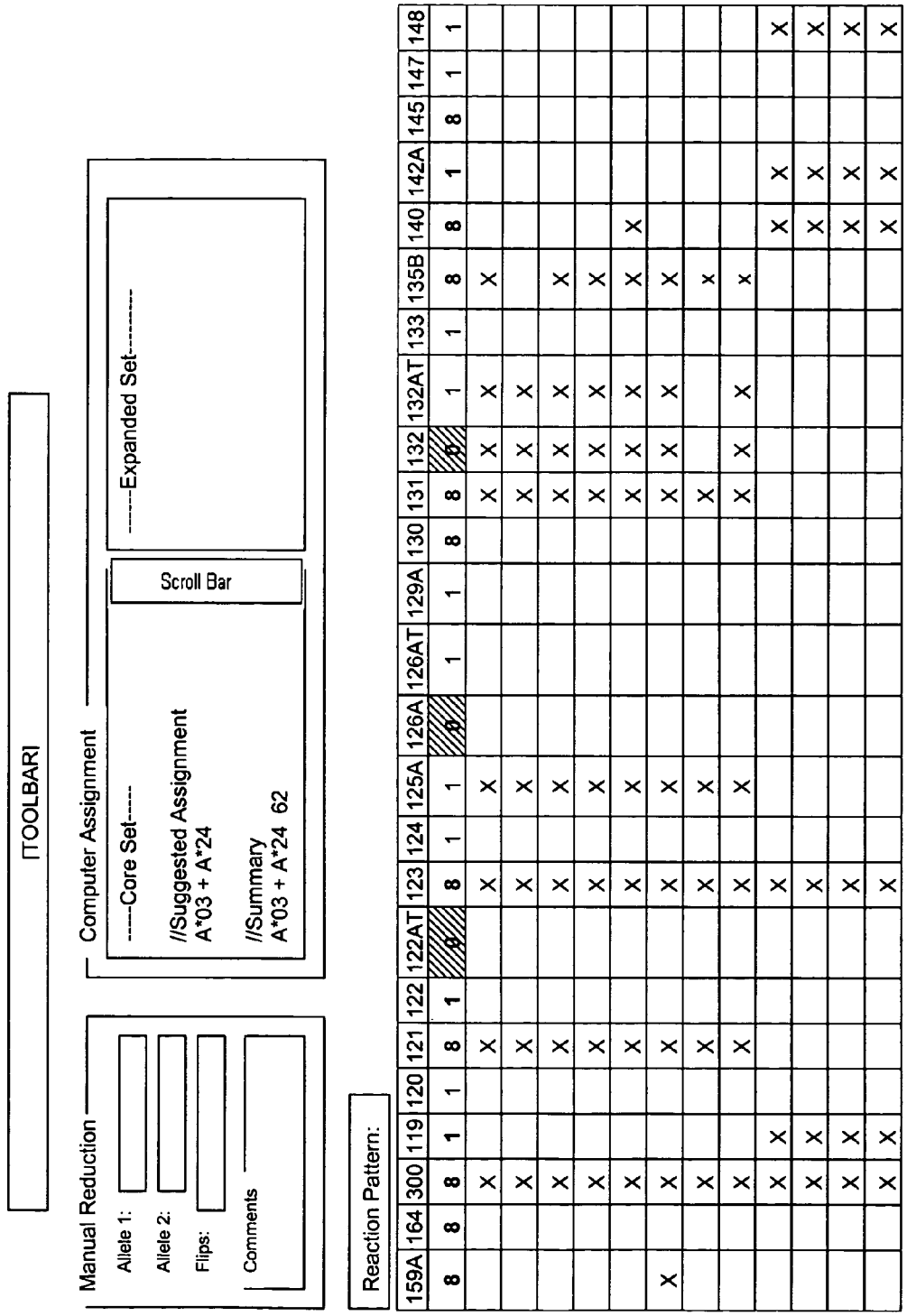
Fig. 3: Allele assignment

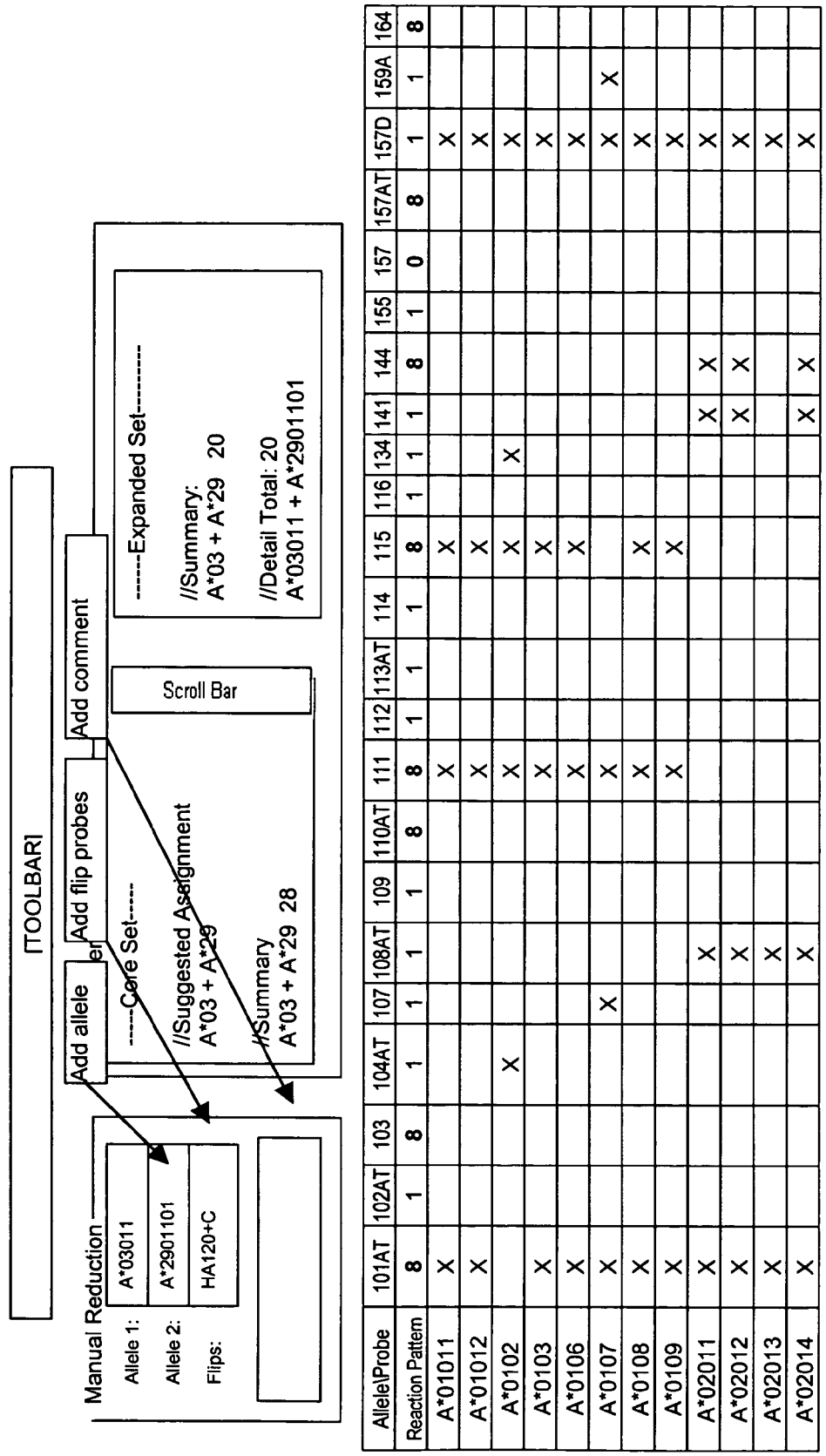
Fig. 4: Allele assignment with manual redaction

Search Criteria
Sample Name:                [MENU]

| HLA-A | | | | | | | | | |
|---|---|---|---|---|---|---|---|---|---|
| Panel Name | Sample Name | Position | Allele1 | Allele2 | # Group | # Allele | Flips | Flip Probe | Warning Message | Comments |
| 3250443 | D020157 | A2 | A*24(02101) | A*26(01) | 1 | 45 | 0 | | | OK |
| 3250443 | D020169 | B2 | A*02011 | | 0 | 0 | 0 | (HA163+D)(Manual) | | |
| 3250443 | D020181 | C2 | A*01(011) | A*29(01101) | 1 | 25 | 0 | | | okay |
| 3250443 | D020193 | D2 | A*3001 | | 2 | 2 | 0 | | | |
| 3250443 | D020205 | E2 | A*26(01) | A*30(01) | 1 | 4 | 0 | | | |
| 3250443 | D020217 | F2 | A*01(011) | A*03(011) | 1 | 31 | 0 | | | |
| 3250443 | D020229 | G2 | A*01(011) | A*29(01101) | 1 | 25 | 0 | | | |
| 3250443 | D020241 | H2 | A*01(011) | A*32(01) | 1 | 10 | 0 | | | |
| 3250443 | D020158 | A3 | A*0302 | A*58(011) | 1 | 2 | 0 | | | |
| 3250443 | D020170 | B3 | A*01(011) | A*02(011) | 2 | 91 | 0 | | | okay |
| 3250443 | D020182 | C3 | A*02(02) | A*02(10) | 1 | 71 | 1 | HA157AT+C | | |
| 3250443 | D020194 | D3 | A*03(011) | A*24(02101) | 1 | 62 | 0 | | | |
| 3250443 | D020206 | E3 | A*11(011) | A*3001 | 1 | 7 | 0 | | | |
| 3250443 | D020218 | F3 | A*01(011) | A*03(011) | 1 | 31 | 0 | | | |
| 3250443 | D020230 | G3 | A*01(011) | A*02(02) | 1 | 8 | 0 | | | |
| 3250443 | D020242 | H3 | A*01(011) | A*24(02101) | 1 | 61 | 0 | | | |
| 3250443 | D020158 | A4 | A*02011 | A*58011 | 0 | 0 | 0 | (HA129A-C)(Manual) | | could be OK |
| 3250443 | D020171 | B4 | A*03(011) | A*3001 | 1 | 7 | 0 | | | |
| 3250443 | D020183 | C4 | A*02(011) | A*24(02101) | 1 | 209 | 0 | | | expanded set, OK |
| 3250443 | D020195 | D4 | A*01(011) | | 3 | 26 | 0 | | | |
| 3250443 | D020207 | E4 | A*01(011) | A*02(011) | 1 | 91 | 0 | | | |
| 3250443 | D020219 | F4 | A*01(011) | A*03(011) | 1 | 31 | 0 | | | |
| 3250443 | D020231 | G4 | A*02(011) | A*26(01) | 1 | 71 | 0 | | | |
| 3250443 | D020243 | H4 | A*0302 | A*6901 | 1 | 1 | 0 | | | |
| 3250443 | D020160 | A5 | A*01(011) | A*68(012) | 1 | 32 | 0 | | | |
| 3250443 | D020172 | B5 | A*0205 | A*2402101 | 0 | 0 | 0 | (HA157AT+C)(Manual) | | okay |

Fig. 7

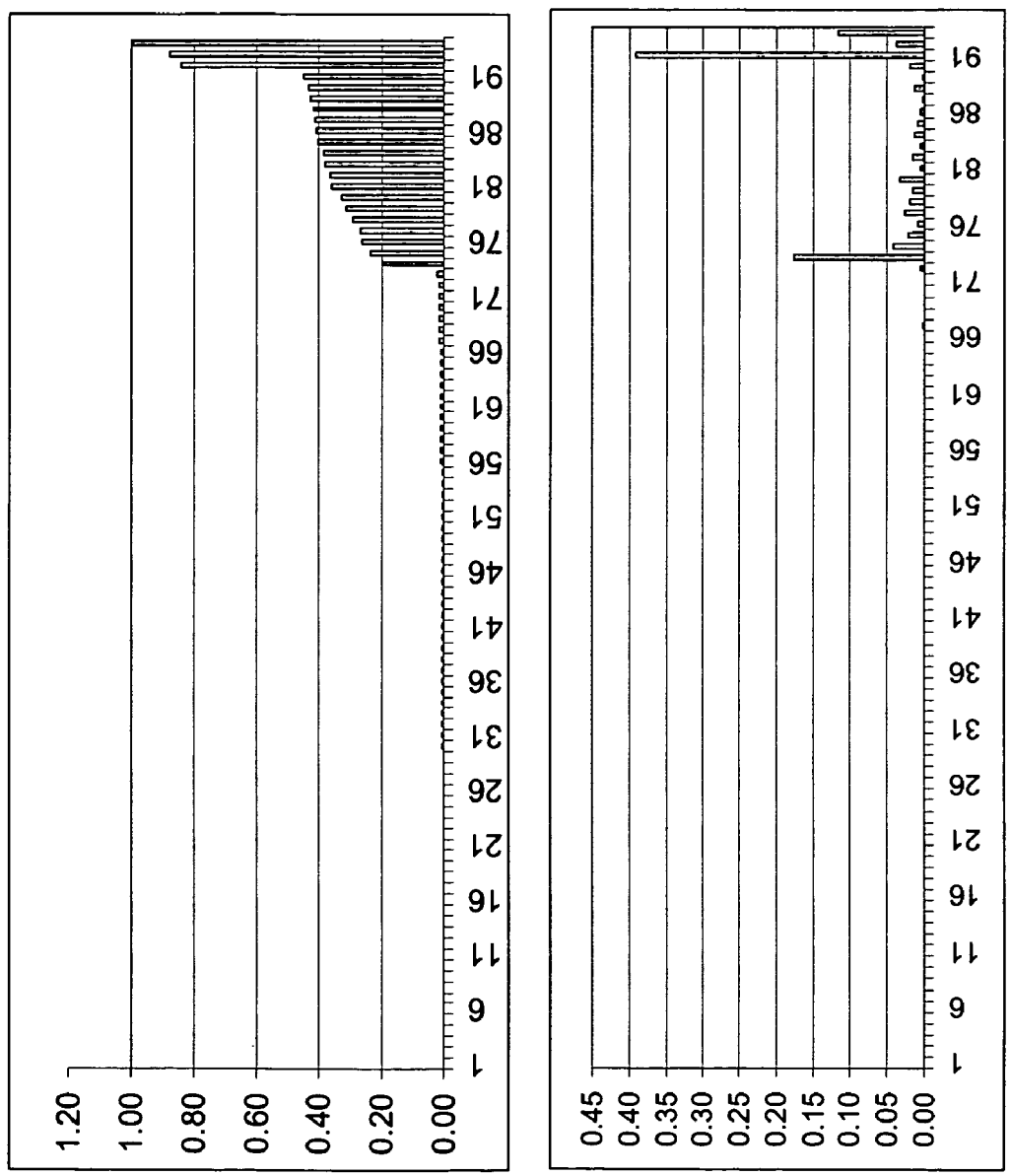
Fig. 8A (upper panel); Fig. 8B (lower panel)

AUTOMATED ANALYSIS OF MULTIPLEXED PROBE-TARGET INTERACTION PATTERNS: PATTERN MATCHING AND ALLELE IDENTIFICATION

BACKGROUND

Complex Interaction Patterns as Diagnostic Markers—Parallel assay formats, permitting the concurrent ("multiplexed") analysis of multiple genetic loci in a single reaction, are well suited to the determination of specific target configurations ("alleles") encountered in a given sample and to the monitoring of quantitative markers such as expression levels of designated genes or levels of circulating protein biomarkers which manifest themselves in receptor-ligand interaction patterns. In what follows, reference to probe-target interactions is meant to refer to this more general situation. By interrogating the target(s) with a selected set of oligonucleotide probes (see, e.g., U.S. Pat. No. 5,837,832, entitled "Arrays of nucleic acid probes on biological chips") and analyzing the patterns of specific interactions of one or more target sequences with that probe set, alleles and allele combinations can be rapidly identified.

This diagnostic capability likely will play an increasingly important role in the study of complex diseases such as arthritis, diabetes and cancer, including the assessment of predisposition to develop a disease having complex inheritance, and requiring the interpretation of an entire set of molecular markers. However, the analysis of the results—in the form of a pattern of intensity readings produced in a multiplexed assay reflecting the strength of interaction of one or more target(s) with the selected set of probes—faces the formidable challenge of interpreting the interaction pattern by mapping it to valid allele combinations or by assessing predisposition or risk, while also ascertaining the reliability and "uniqueness" of the assignment.

A Model: HLA Molecular Typing—The analysis of polymorphisms in the Human Leukocyte Antigen (HLA) gene complex provides a model of the complexity involved in analyzing disease association, thereby serving to delineate the requirements to be addressed by rapid and reliable automated analysis. The HLA complex comprises multiple highly polymorphic loci which encode variable antigens mediating an immune response to "foreign" bone marrow or tissue. At present, 282 HLA-A, 540 HLA-B and 136 HLA-C class I alleles, and 418 HLA-DRB, 24 HLA-DQA1 and 53 HLA-DQB1 class II alleles have been identified. Many known allele sequences appear in public databases, for example, the IMGT/HLA database, www.ebi.ac.uk/imgt/hla/intro.html) for human leukocyte antigens.

Parallel ("multiplexed") hybridization assays of various formats have been widely used for HLA molecular typing which requires a unique combination of throughput and reliability in identifying alleles or groups of alleles associated with specific class I and class II antigens. In the context of HLA molecular typing, standard assay methodologies of the art invoke a "reverse dot blot" format. In accordance with this format, probes, placed, in a set of well-separated bands, on a narrow strip of nylon membrane or other substrate material, are exposed to a solution of target(s) under conditions permitting capture of the target(s) to produce, in a subsequent decoration step, calorimetric signals. Other methods of the art include the use of probes displayed on encoded microparticles which are suspended in a target solution and analyzed by flow cytometry (see "Products" http://www.onelambda.com). A recent method provides an integrated assay environment by using planar arrays of encoded microparticles arranged on silicon chips (see, e.g., allowed application Ser. No. 09/690,040, assigned to BioArray Solutions, Ltd.).

The design of parallel assay formats for the analysis of polymorphic loci such as the HLA complex, notably the selection of sets of primer pairs and probes, has been described in the prior art as well as in several co-pending applications (see, e.g., Concurrent Optimization in Selection of Primer and Capture Probe Sets for Nucleic Acid Analysis," filed Jul. 15, 2004 and assigned to BioArray Solutions, Ltd.).

Sequence Complementarity and Binary Representation—The interpretation of probe-target interaction patterns involves the task of matching a binary string ("reaction pattern") derived from an experimental signal intensity pattern to one (or more) allele combinations or establishing the validity of new alleles.

Each allele will have subsequences that are perfectly complementary, and others that are not complementary to probes in a probe set constructed to interrogate the target. This configuration is represented in the art by a binary code which provides the basis for allele assignments. That is, by assigning to each perfectly matched probe a score "+" (herein denoted by "8"), and to each mismatched probe a score of "−" (herein denoted by "1"), a binary string is constructed to represent the pattern of interaction of the chosen probe set with a specific combination of alleles encountered. The dictionary showing the correspondence between alleles and binary strings is known in the art as the "hit table".

The reaction pattern—produced by the selected set of probes—may correspond to more than a single allele combination, and the degree of ambiguity ("degeneracy") determines the precision ("resolution") attainable in identifying allele combinations. In general, the degree of resolution can be increased by adding probes to the set.

Assay signal intensities reflect the strength of probe-target interactions. An ideal probe produces an assay signal of high intensity when perfectly complementary ("matched") to its target subsequence in a given sample and otherwise produces an assay signal intensity of low intensity. That is, the signal intensity distribution of such a probe over a large sample set, ideally would display two distinct peaks, suggesting a segmentation of signal intensities into subpopulations reflecting "matched" or "mismatched" probe and target sequence configurations.

However, in practice, the interaction of one or more polymorphic target with a multiplicity of probes can produce a wide range of assay signal intensities. For example, otherwise positive assay signal intensities may be reduced, or otherwise negative assay signal intensities may be enhanced, thereby "smearing out" the individual distributions of intensities. For example, probe-target hybridization is weakened when a probe encounters in a target subsequence an allele comprising polymorphisms other than the probe's "designated" polymorphism. Conversely, a probe-target hybridization may be unexpectedly enhanced when a probe, while displaying a significant mismatch with the target within its designated subsequence, matches a specific allele in a non-designated subsequence.

As with binarization generally, subpopulations are delineated by selection of a threshold. Particularly when assay signal distributions are not bimodal, threshold selection represents a critical initial step in the analysis.

In the context of HLA molecular typing, the requisite extensive analysis of interaction patterns and assignment of alleles currently relies to a substantial degree on the experience of specialists. These specialists and experts engage, usually with minimal computational support, in a time-consuming, difficult and often subjective process of interactively establishing, reviewing and editing ("redacting") allele assignments, often with reference to printed compilations of known alleles (e.g., the database maintained by the National Marrow Donor Program) and corresponding "hit tables."

As with molecular typing of leukocyte antigens and erythrocyte antigens, the reliable and rapid analysis and interpretation of complex probe-target interaction patterns represents a prerequisite for the meaningful validation of sets of genetic markers to validate these "predictors" of disease predisposition or treatment responsiveness in patient populations of sufficient size to permit statistically significant conclusions. Similar challenges arise in other areas, for example: in connection with the analysis of genetic polymorphisms in mutation analysis for carrier screening and diagnosis and associated risk assessment; and in connection with the assessment of predisposition to acquire genetic diseases of complex inheritance which may manifest itself in the form of an entire set of polymorphic markers or gene expression profiles.

A convenient software system invoking computational algorithms and robust procedures for automated pattern analysis and interpretation, and providing an integrated environment for the interactive review and redaction of assignments as well as data management and visualization would be desirable.

SUMMARY

Disclosed are methods and algorithms (and their implementation) supporting the automated analysis and interactive review and refinement ("redaction") of the analysis within an integrated software environment, for automated allele assignments. The implementation, preferably with a software system and a program referred to as the Automated Allele Assignment ("AAA") program, provides a multiplicity of functionalities including: Data Management by way of an integrated interface to a portable database to permit visualizing, importing, exporting and creating customizable summary reports; System Configuration ("Set-up") including user authorization, training set analysis and probe masking; Pattern Analysis including string matching and probe flipping; and Interactive Redaction combining real-time database computations and "cut-and-paste" editing, generating "warning" statements and supporting annotation.

Thresholding—Methods of selecting and refining thresholds are disclosed, including a generalization of the binary representation obtained by segregating probe intensity distributions into three or more subpopulations.

Initial Threshold Determination—A method of setting thresholds by way of analyzing a reference ("training") set and selecting is also disclosed, for each probe in a selected probe set, a threshold which maximizes the degree of concordance of assay results and assigned alleles with those provided for the training set. The method of determining the initial threshold settings also provides a figure of merit ("goodness") as the basis method of assessing the robustness of that threshold. A related method of initial threshold determination disclosed herein applies a binarization algorithm to individual probe intensity profiles.

Threshold Refinement: Pattern Matching—A method of refining thresholds by matching an experimental binary string ("reaction pattern") is disclosed, produced by application of initial threshold settings, with a compendium of reaction patterns corresponding to valid allele combinations. The software system herein supports a mode of altering ("flipping") specific bits within the experimental string ("word"). The program identifies probes, and probe combinations, as candidates for "flipping" in order to produce complete or partial concordance between the modified experimental "word" and the closest word, or words, in the dictionary. Flipping of a probe—for certain samples in the set under consideration—corresponds to a refinement in the threshold setting for that probe.

Probe Masking—Also disclosed is a program feature supporting a configuration ("set-up") mode in which selected probes can be temporarily excluded from analysis ("masked"). Assay signals produced by probes which do not contribute significantly to discriminating among alleles—or may be judged to produce intensity patterns of low reliability—can also be masked when analyzing the results, and then viewed only if their contribution is deemed necessary.

Allele Frequency Statistics—In another aspect, the software system provides a method for tracking and displaying the relative frequency of occurrence of allele groups (and combinations thereof).

Interactive "Redaction"—The software system provides an integrated environment to facilitate simultaneous access to the data being analyzed and databases and hit tables being consulted, for example in the course of redaction. "Cut-and-Paste" operations are provided in multiple screens to permit the rapid and convenient editing of automated ("program") assignments including an annotation function.

Confirmatory Testing for Resolution of Ambiguity—The program also accommodates additional information aiding in the resolution of ambiguities by way of group-specific amplification or by way of using elongation mediated analysis of polymorphisms (see "Multiplexed Analysis of Polymorphic Loci by Concurrent Interrogation and Enzyme-Mediated Detection" filed Oct. 15, 2002; Ser. No. 10/271,602).

Distributed Analysis: Processing, Analyzing, Interpreting, Archiving—The architecture of the software system supports a mode of distributed analysis, permitting different functions such as assay image recording, automated analysis, interactive redaction, and assessment and final "sign-off" and report generation to be performed by different individuals in different geographic locations. This mode of distributed analysis expands the capabilities of individual testing laboratories to expand their respective test menus without the requirement for local expertise pertaining to the many disparate areas of expertise. For example, testing center locations may be chosen so as to facilitate collection of patient samples, while board-certified physicians may review and release final test results from a different location, while serving multiple testing centers.

Also disclosed is a method and pseudocode for fully automated allele analysis, which is set forth below.

BRIEF DESCRIPTION OF THE DRAWINGS

FIG. 1B shows a threshold determination for one probe in a training set of probes, where the threshold value is plotted on the X axis, and the threshold measurement is on Y axis. The optimal threshold yields the maximum measurement in Y, which is 1 in this case.

FIG. 1C shows the system settings for a number of different HLA probes. The allele assignment tolerance (see FIG. 2) is entered in the text boxes. HLA-A is allowed a maximum 6 flips; HLA-B 8 flips; and HLA-DR 5 flips. Each probe can be assigned as required, high confidence, low confidence or not used. The core set of probes (see FIG. 3) consists of only the high confidence probes, while the expanded set of probes includes the high and low confidence probes. By changing the settings, one can interactively change the core set and expanded set. For instance, HA120 can be set as high confidence and HA121 as low confidence.

FIGS. 2A to 2C show, respectively, the normalized intensity ("ratio") for the probes HB103, HB123A, HB154, sorted in the order of increasing ratio to illustrate a discontinuity in the probe ratio profile. HB103 (FIG. 2A) has the largest difference in ratio profile. HB123A (FIG. 2B) has no obvious jump in profile. HB154 (FIG. 2C) has two jumps in the profile. In the reaction pattern, 8 indicates positive, 1 indicates negative (no signal) and 0 indicates the probe is not used.

FIG. 3 is an example of allele assignment, where the reaction pattern is shown in the first row, ranging from 0 to 8, and the hybridization string is the pattern shown in the columns. The columns 119, 121, 122, 135A, 142A and 145 are low confidence probes. Since there is only one suggested assignment, the expanded probe set is empty.

FIG. 4 is the reaction pattern and hit table for an exemplary reaction between probes and a target, showing also the screen shot of the program for performing manual redaction, allele assignment, and a place for inserting comments.

FIG. 7 is a screen shot illustrating the assignment summary information for a panel designated "03250443," and includes the panel name, sample name, sample position, allele assignment, flip probes, warning message and comments.

FIG. 8A is a probe ratio profile.

FIG. 8B is the numerical derivative showing the inflection points derived from FIG. 8A.

DETAILED DESCRIPTION

Figure 1A:
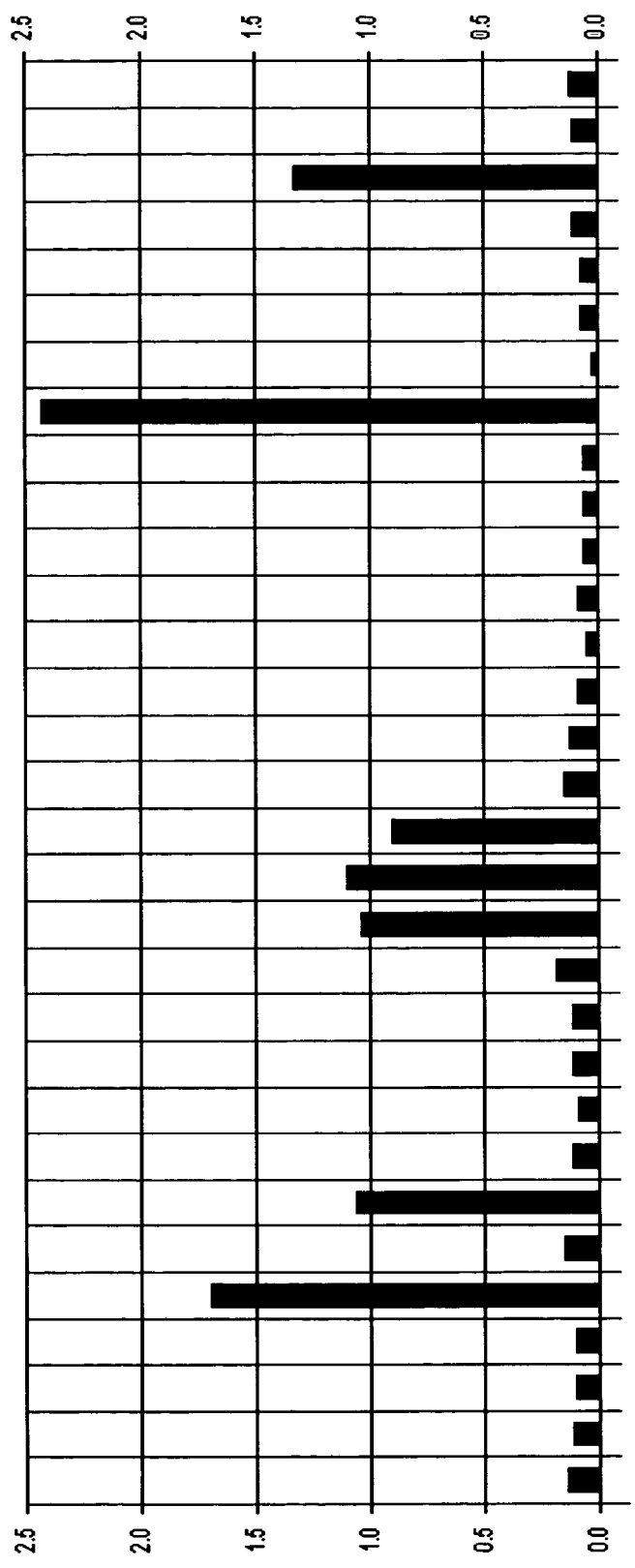
FIG. 1A illustrates a set of assay signal intensities recorded for probe HA109 in the analysis of a training set of samples. By an independent method, the normalized probe intensity was scored negative for samples marked "−" and positive for samples market "+".
Figure 5:
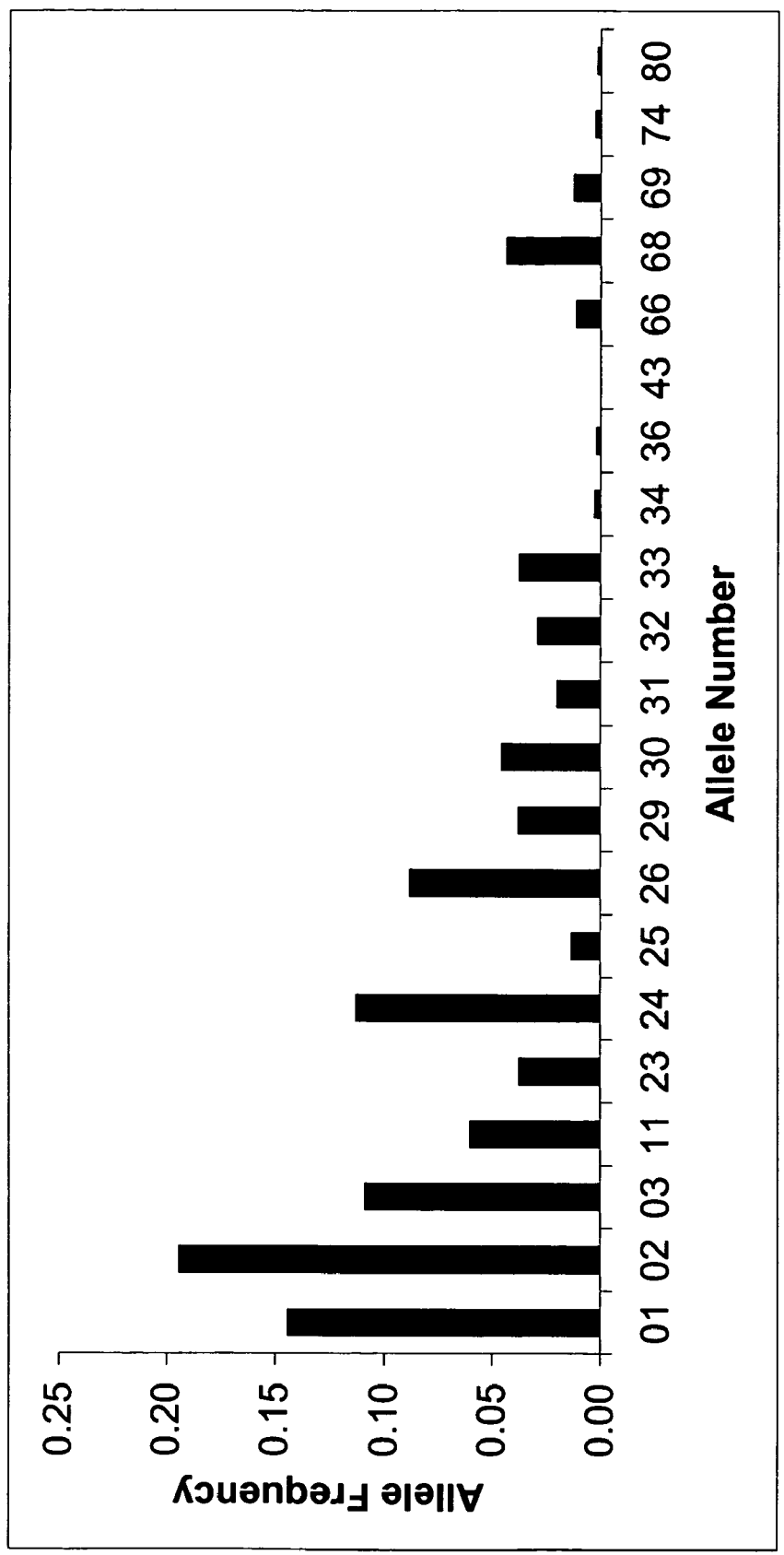
FIG. 5 is a bar-graph for the allele frequency distribution of a particular population.
Figure 6:
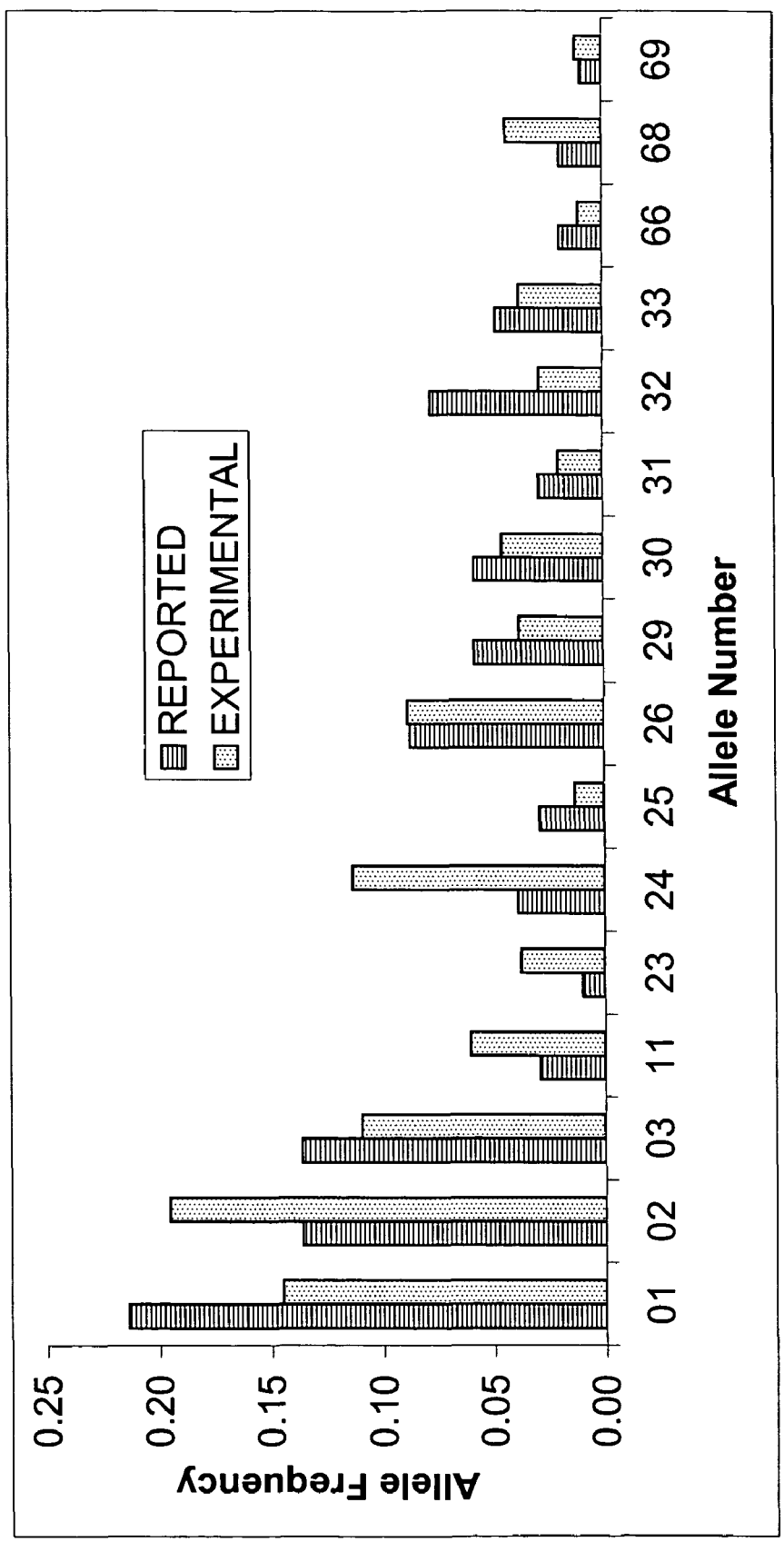
FIG. 6 is a bar-graph showing the comparison between reported genotyping studies of a allele distribution in a "Jewish Normal" population, and the experimental results for such population.

Following the recording of an assay signal intensity pattern for a given sample, a sequence of analytical steps is performed to identify the corresponding allele combination.

2.1 Conversion of Assay Intensity Patterns into Binary Strings

Normalized Assay Signal Intensities: Probe Intensity Profiles—Certain methods of probing polymorphisms within a target nucleic acid such as Elongation-mediated Analysis of Polymorphisms (eMAP™, also referred to herein as "capture-mediated elongation"), disclosed in co-pending U.S. patent application Ser. No. 10/271,602 (PCT/US02/33012) produce assay signals which rely on a molecular recognition process whose high specificity produces an approximately "binary" distribution of assay signals. In contrast, methods such as Hybridization-mediated Multiplexed Analysis of Polymorphisms (hMAP™, U.S. patent application Ser. No. 10/847,046) produce assay signal intensities reflecting the effective affinity governing the interaction of each probe in a set of multiple such probes with the target. To correct for variations in background, original target concentration or other experimental conditions, experimental signal intensities recording probe-target interactions are normalized using signals recorded from positive and negative control probes (and probe-target pairs) included in the reaction.

From each signal intensity, usually the mean value, $I_k$, for the k-th type of probe, including the positive control signal, $I_{PC}$, and the negative control signal, $I_{NC}$, is subtracted, and the result is divided by the corrected positive control signal to obtain a normalized intensity (ratio):

$$r=(I-I_{NC})/(I_{PC}-I_{NC})$$

To facilitate an assessment of the performance of any given probe in the panel, a probe intensity profile, also referred to herein as a ratio profile, is constructed by sorting the r-values recorded for that probe over a set of samples, typically 100 samples, for example, in ascending order. Examples of such profiles are shown in FIGS. 2A-2C, where FIG. 2A illustrates a profile displaying an abrupt transition of large amplitude from lower to higher r-values, whereas FIG. 2B illustrates a profile displaying a gradual transition of small amplitude.

For methods such as hMAP, the normalized signal intensities are first converted to a binary representation: if r exceeds a pre-set threshold, T, the corresponding binary score is positive, s=1 (also denoted herein as "8"), otherwise negative, s=−1 (also denoted herein as "1"). Methods of implementing this critical signal processing step are disclosed in the following subsections.

2.2 Determination of Thresholds: Binarization—An algorithm is disclosed for the determination and iterative refinement of binarization threshold settings. As is true for the analogous step in image analysis of converting gray-scale pixel intensities to "black- and white" representation, binarization assigns normalized assay signal intensities to one of two subsets. This is unproblematic as long as the distribution of normalized signal intensities for a set of samples under consideration has a bimodal shape featuring well separated peaks: a threshold can then be placed almost anywhere between the two peaks without affecting the result; FIG. 2A corresponds to a bimodal histogram. However, in other cases, when separate peaks are not clearly resolved, binarization presents a source of uncertainty or potential error: the assignment of specific intensity values to one or the other subset will depend in a sensitive manner on the precise placement of the threshold; FIG. 2B corresponds to such a case.

Initial Threshold Settings: Analysis of "Training" Sets—Initial threshold settings can be based on the analysis of a reference or "training set". Preferably, reference samples are chosen to reflect characteristics of the group of samples of interest; for example the prevailing frequency of occurrence of allele combinations and haplotypes. Such information can provide additional constraints on likely allele assignments. Methods of automated collection and statistical analysis of sample population statistics are elaborated below.

A reference ("training") set of S samples, with independently determined and validated reference reaction pattern $\{\sigma_k, 1 \leq k \leq P_T\}$, and independently determined and validated allele assignments, is analyzed with a selected set of P probes, to obtain the normalized intensity (ratio) pattern $\{r_k; 1 \leq k \leq P\}$, and, for each probe, k, in the selected set (see also below), a threshold, $T_k$, is determined so as to maximize the concordance between the actual reaction pattern, $s_k=s_k(T)$, and the reference pattern $\{\sigma_k, 1 \leq k \leq P_T\}$.

That is, for each probe in the actual set, a threshold is determined for each probe by analysis of the normalized intensity profile over the training set of S samples so as to maximize the cross-correlation $C=\Sigma_i((r_i-T_k)*\sigma_i)/\Sigma_i|(r_i-T_k)|$, $1 \leq i \leq S$. For each probe in turn, to find the maximum of the function C, the threshold setting, $T_k$, is increased stepwise until the sign of the quantity $r_i-T_k$ matches that of the corresponding bit, $\sigma_i$, in the reference pattern. For probes used in the assay, but not in the interrogation of the training set, a reaction pattern is "back-calculated" from the hit table using the assigned alleles. FIG. 1B illustrates the shape of the function $C=C(T)$, $r_{min} \leq T \leq r_{max}$. The threshold setting is chosen so as to maximize the function C.

The pseudocode for determining the initial threshold setting is as follows:

```
/*
** ρ is the normalized intensity ("ratio") pattern for a given sample; binarization will
** convert each intensity pattern into a reaction pattern composed of P bits; there will
** be S such patterns;
** π is the set of probe profiles; there will be P such profiles, each with a threshold,
T;
** τ is the set of optimal (initial) thresholds, to be determined by maximization of C; */
GenerateProbeProfiles(ρ, S, π, P)          /* sort reaction patterns by probe
*/
{
    FOR( each probe )
    {
        ExtractIntensity( from reaction patterns )
        SortProbeIntensities( );
    }
}
/*
** maximize C = Σᵢ ((rᵢ – Tₖ) ∗ σᵢ) / Σᵢ |(rᵢ – Tₖ)|
** the rᵢ denote the elements of the ratio profile R */
*/
FindThreshold(R, Σ, S)
{
    C_max = 0;
    T = r_min;
    DO
    {
        IF( (C = Σᵢ ((rᵢ – T) ∗ σᵢ) / Σᵢ |(rᵢ – T) |) > C_max) C_max = C;
        T = T + ΔT;
    }WHILE( T <= r_max );
    Return( T );
}
DetermineInitialThresholds( )
{
    GenerateProbeProfiles(ρ, S, π, P)
    FOR( each of P ratio profile, πₖ )
    {
        τₖ = FindThreshold( πₖ, Σₖ, S )
    }
    Return(τ);
}
```

"Goodness" of Threshold Settings—Threshold settings may be robust for some, but less robust for other probes in the set. That is, when the composition of the two sample subpopulations, generated by application of a threshold T to the probe intensity profile changes in response to a small change in the value T to $T+\Delta T$ or $T-\Delta T$, where $\Delta T/T \ll 1$, then that threshold is not robust, and the statistical confidence is low.

To permit the placement of confidence intervals on individual threshold settings, a figure of merit ("goodness of threshold") also is disclosed herein. This is derived from the shape of the peak of the function $C=C(T)$, produced in the course of maximizing the cross-correlation with a set of assignments for a training set. The steeper the peak in the function, the more sensitive the selected value of T to small variations in T, as illustrated in FIG. 1B.

A "goodness", G, of a threshold selected by the method of maximizing the cross-correlation, C, as just described, is defined as follows:

$$G=(C_L+C_R)/2C_{Max},$$

wherein $C_{Max}$, $C_L$ and $C_R$ respectively denote the maximum value of C, $C_L$ the value of C obtained when decreasing the threshold value by 30%, and $C_R$ the value of C obtained when increasing the threshold value by 30%.

Weights—Once a threshold, T, has been determined, the probe intensity profile, $\{r_i, 1 \leq i \leq S\}$ can be recast into a scaled form, $w_i=(r_i-T)/T$, wherein the weights, $w_i$, represent the relative magnitude of individual (normalized) signal intensities. The software system described herein (designated "AAA") tracks weights and displays them in one of several formats, for example, by a simple classification into "Close" ("C", $w \leq 0.5$) or "Distant" ("D") in connection with bit "flipping", as further discussed below.

2.3 String Matching: Correlations within Probe-Target Interaction Patterns

The analysis of experimental intensity patterns aims to identify, or approximately identify, the underlying target allele(s). To that end, intensity patterns are binarized by application of a set of thresholds, and the resulting binary string ("reaction pattern") is compared to combinations of pairs of such strings corresponding to known alleles listed in a "hit table." Each entry in a "hit table" represents a valid allele and provides a binary sequence in which each position contains a score of "Matched" or "Mismatched" referring to the degree of complementarity of the allele with the probe in that position (see FIG. 3A). Alleles are designated by 4-digit codes and are grouped by the leading 2-digits into antigen groups.

Error Correction by String Matching: "Flips"—To identify the target alleles, the binary reaction pattern, $\{s_k, 1 \leq k \leq P\}$ is compared, bit by bit, to all reference strings representing 2-allele combinations; these are generated by application of an OR operation to the hit table entries. The matching of entire bit strings enforces correlations and affords a method of "error correction" by way of inverting ("flipping") individual bits in the string as judged necessary in order to produce a match with a valid reference string. This process is akin to checking typographical errors so as to produce valid words: by changing the letter "t" in "valit" to "d", a valid English word is obtained; another valid English word is obtained by changing "i" into "u" and "t" into "u", but "valit" is "closer" to "valid" than it is to "value", and the former therefore more likely represents the desired word.

In analogous manner, the AAA program is designed to find the closest valid bit strings ("words") representing valid alleles, as identified, for example, in a database which can be entered in the AAA program. The AAA program lists the "closest" valid strings, grouped by common 2-digit "group" codes, in the order of increasing Hamming distance (i.e., the number of mismatched bits) from the experimental string. Specifically, the program identifies the mismatched bits and suggests the requisite "flips", namely "1 to 8" or "8 to 1," which would produce a complete match between the experimental string and those additional valid strings within a preset maximal Hamming distance.

The AAA program also permits a deeper search of the space of reference strings in order to produce a list of "near-matches" (see drop-down menu illustrated in FIG. 4). This extended analysis frequently reveals possible alternate strings representing more likely allele assignments based on such additional considerations as the frequency of occurrence of certain alleles or haplotypes in the population of interest. This feature substantially reduces the time and effort expended on interactive editing.

Distance between Strings—Within each group, strings corresponding to valid allele combinations are ranked in the order of an increasing weighted Hamming distance from the reaction pattern. This distance function is defined in terms of the weights, $w_i = r_i - T)/T$, associated with the mismatched probes. For example, assuming there to be M mismatched probes, a possible distance function is:

$$X^2 = (1/M) \Sigma_{mismatched\ probes} w^2$$

2.4 Iterative Threshold Refinement

Ideally, the string matching procedure just described will produce an unambiguous match between the reaction pattern and a string representing a valid allele combination. However, even when a perfect match is called, this call may not be unambiguous if it involves low weights for one or more of the probes. That is, in practice, the reaction pattern may contain false negatives or false positives, depending on the threshold setting for individual probes and the weights of normalized intensities. Especially the statistical confidence associated with threshold settings of probes having continuous ratio profiles for the set of samples under consideration will be low, and it is therefore beneficial to have a process of adjusting ("fine tuning") such threshold settings.

The string matching procedure provides a basis for the refinement of initial thresholds. After all, flipping a probe is equivalent to adjusting the corresponding threshold so as to change the sign of the normalized ratio relative to the threshold setting. That is, if, following an initial pass of automated allele assignment for a set of samples, a certain probe is consistently "flagged" as either false positive or false negative, this is an indication that a threshold refinement for that probe is in order. Accordingly, threshold optimization involves an iterative process of adjusting the threshold settings of one or more "flagged" probes so as to minimize the total number of flips identified by the AAA program. Because this threshold optimization process is based on string matching, rather than on the inspection of individual probe ratio profiles, as in the step of setting initial thresholds, threshold optimization reflects the correlations between multiple probes in the set and improves statistical confidence. Threshold refinement can be performed on a continuing basis using analyzed samples as a continually expanding reference set. In this application, each new set of samples becomes a new training set.

In general, the number of flips even after threshold optimization will remain finite. In such cases, the weights associated with indicated flips must be taken into account. The AAA program conveniently designates ratios of "flips" as either "Close" (C, $r \leq 0.5$) to threshold, or "Distant" (D) from threshold. The cut-off represents a tunable performance parameter which may be set more or less conservatively, a more conservative setting generally implying a greater degree of interactive review and editing, as discussed in greater detail below. A requirement for flipping "distant" probes, i.e. those having a large weight, in order to obtain a match represents an indication that a new allele may be in hand.

The pseudocode below summarizes the threshold refinement procedure as implemented in the AAA software system of the invention.

```
/* calculate allele assignment for a list of samples, then
/* identify and analyze the flipped probes for that list
    CalculateAssignment(SampleLists);
    GetFlips(SampleLists);
    AnalyzeFlips( );
/* Select probes requiring threshold refinement
    ProbeSet = SelectProbes( );
/* for each probe, find the optimal threshold by minimizing the number
of total flips
    FOR each(probe in ProbeSet)
    {
        T_0 = GetInitialThreshold(probe);           /* get initial
                                                       threshold
        FOR( T = T_0_range; T<= T_0+range;
        T+=deltaT)                                   /* adjust threshold
        {
            RecalculateAssignment(SampleLists);
            TotalFlips = AnalyzeFlips( );            /* re-analyze flipped
                                                       probes and get the
                                                       number of total
                                                       flips
        }
        FindMinTotalFlips( );                        /* find min total
flips
        /* the new threshold will be the one minimizing total flips
        T_new = GetNewThreshold(probe);
    }
```

Additional features included in the AAA software system are set forth below.

Modification of Probe Sets—A particular binary reaction pattern may match with more than one allele, and often will if the bit string has only a few elements ("8s" and "1s") and the target includes multiple polymorphic regions. The degree of ambiguity is calculated by simply enumerating the number of unresolved ("degenerate") alleles. Lengthening of the string, by inclusion of additional probes, can provide a means to attain increased resolution in order to resolve ambiguities.

Probe Masking: Core and Expanded Probe Sets—Described below is a method for interactive designation of core sets and expanded sets of probes, along with a "probe masking" feature, which can be used to correct for signals from those probes which do not perform as well as others. In probe masking, results from those probes which hybridize to a wide variety of samples, rather than only to particular samples with particular alleles, are ignored. Such a wide level of hybridization may result from cross-hybridization or from probes targeting widely expressed subsequences.

The AAA software system provides a configuration ("setup") screen permitting the user to designate probes within a panel to be part of a core set or an expanded set. The probe-masking function prompts users to enter a list of probes which are to be ignored ("masked") in the first pass of automated allele assignment—that is, the program calculates assignments first on the basis of a core set of probes which hybridize more narrowly. The objective of using the core set is to obtain a group-level assignment for alleles (i.e., a group of several possible alleles) using probes which provide group level discrimination with a high confidence level.

In the probe masking mode, the AAA program first performs group-level assignments using only the core set of probes. In an (optional) second pass, the assignment can be refined by repeating the calculation with the extended set which contains all the probes in the core set, as well as the remaining less-reliable probes. The second pass will produce additional assignments that remain compatible with the assignments made in the first pass. The program also performs this second pass whenever the first pass does not produce a unique group level assignment.

The extended set is useful in guiding "redaction" and allows the user to select the most likely allele assignment. In some cases, the complementary (e.g., antisense) version of one or more probes (and the corresponding transcripts or amplicons) may need to be generated and used, to avoid excessive cross-hybridization. In such cases, the non-complementary probes are then excluded from the first and/or second pass.

Population Statistics: Analysis of Allele Frequency Distribution—The rate of recurrence of each allele is dependent on the population over which HLA typing is being conducted. For a panel containing a large number of samples, the occurrence of a particular allele is representative of its abundance or rarity in the entire population of interest. The distribution of alleles in a population of known ethnicity can be calculated for a panel.

The results for a set of panels from the AAA database program were used to calculate allele frequency. The program assigns each sample a set of two alleles based on its reaction pattern over the whole probe set. The frequency calculations are based on two digit allele assignments. The first two digits of the allele assignments for all samples are extracted and compiled into a single vector. A histogram is calculated which lists each allele with the number of times it is encountered in the panel (its count). The frequency is calculated as the count is normalized by the total number of assignments.

One purpose of tracking allele frequency statistics, as implemented in the program, is to provide editing aids, such as warning flags whenever a rare allele is identified. This will help in case of degenerate assignments, where more than one unique assignment is possible. In such cases, those assignments which involve rare alleles can be eliminated manually. In case of single assignments, such flagging of rare alleles ensures that the assignments are manually checked, and either verified, or flipped.

Interactive "Redaction"—Following automated allele assignments using the program and the methods described above, the putative assignments may be "edited" against either an allele database indicating known alleles, or by a combination of experimental data for alleles (which forms a continually expanding reference set) and an allele database. An illustration of key steps is given in an Example.

Weights represent a measure of confidence in the bit assigned any given probe intensity: bits are less likely to be incorrectly assigned, and flips therefore are less likely to be executed, the larger the weight of a specific probe intensity signal (or a suitable function based on those weights). Thus, weights can help guide interactive redaction.

Another guide is available in the form of allele frequencies in the entire population, or in a sub-population being monitored. Again, the analyzed samples form a continually expanding reference database, which are added to the training set whose allele (and haplotype) frequencies are updated in real-time.

Detection of New Alleles—New alleles may be indicated by targets which produce binary reaction patterns which can be matched to existing reference strings representing combinations of known alleles only by flipping probes having significant weights. This is discussed in greater detail in Example I (Allele Assignment) below.

Generalization of Binary Representation—The AAA program also accommodates representations of intensity patterns other than the binary representation and the corresponding binary strings ("words").

Three-Letter Alphabet and Hit Tables—As an immediate generalization, consider representations invoking an alphabet of three or more letters. Such a three-letter representation naturally arises when a pair of degenerate probes is provided for one or more of the designated polymorphic target sites. For example, in a novel approach invoking the format of Elongation-mediated Multiplexed Analysis of Polymorphisms (eMAP) to analyze mutations in a set of genes encoding human blood group antigens, a pair of degenerate elongation probes is provided for each of the designated variable sites. The members of the pair differ at or near their 3'termini, one member designed to match the expected normal target allele, the other member designed to match the expected variant allele. Only the elongation probe matching the target is elongated in a manner producing a corresponding assay signal associated with the elongation products (see U.S. application Ser. No. 10/271,602). That is, eMAP produces one of three possible values at each designated polymorphic site, namely normal, variant ("homozygous" mutant), or heterozygous.

The representation reflects the three possible outcomes of the eMAP determination at each designated site, namely:
  normal probe matched, variant probe mismatched: normal—denoted by 1
  normal probe mismatched, variant probe matched: variant—denoted by $-1$
  normal probe matched, variant probe matched: heterozygous—denoted by 0

This reflects the possible combinations of the underlying alleles, namely AA (normal or "wildtype"), BB (variant, homozygous) and AB or BA (heterozygous). A hit table for the sites of interest will be composed of letter codes which are combined by the rules just stated.

Example III illustrates the use of a 3-letter alphabet (1, 0, $-1$) to represent observed biallelic combinations.

Upper and Lower Thresholds—A three letter representation also arises, in analogous manner, in connection with the introduction of an upper and a lower threshold. For each probe under consideration, an assay signal intensity below the lower threshold corresponds to a mismatch with both target alleles, an assay signal intensity above the lower, but below the upper threshold corresponds to a match with one, but not the other allele, and an assay signal intensity above the upper threshold corresponds to a match with both alleles.

The designation of negative and positive bits can be made with increased confidence if two thresholds, which segregate normalized assay intensities recorded for any given probe into three sub-populations, are defined. The three sub-populations would be those for which: (i) a given probe is mismatched to both assigned alleles (1,1), (ii) a probe is matched to one allele (1, 8; 8, 1), and (iii) a probe is matched to both alleles (8, 8).

Because of the possible existence of the second (8, 8) threshold, it would be possible to establish a threshold for a particular probe incorrectly; that is, the threshold for a (8, 8) probe as distinguished from a (8, 1) probe, could be incorrectly identified as the threshold for a (8, 1) probe distinguished from a (1, 1) probe. Such incorrect threshold designations can be spotted and corrected by continued refining and expansion of the training set, and/or by double-checking the allele assignments against the known allele database references and ensuring consistency.

Another situation in which needs to be considered, is that normalized assay intensities recorded for any given probe which are above the second (highest) threshold, could be due to reaction with the designated target subsequence on both alleles (indicating a homozygote), or could be due to reaction with two independent alleles, which coincidentally, are reactive with that probe. Again, this situation can be spotted and corrected by continued refining and expansion of the training set, and/or by double-checking the allele assignments against the known allele database references.

In determining the location of thresholds, where there is more than one threshold for a particular probe, one can examine the ratio intensity profiles (as shown in FIGS. 2A to 2C; see also FIGS. 8A and 8B). But if there is no sharp inflection in the profile, as illustrated clearly in FIG. 2B, one can locate the inflection points, and thus the thresholds, by taking the numerical derivative using a convolution filter. The results of taking the numerical derivative in this manner is shown in FIG. 8A, which is a ratio profile, and FIG. 8B, which is the numerical derivative showing the inflection points derived from FIG. 8A.

Digitization of Analog Patterns—Normalized intensities, instead of being binarized, also can be digitized with any desirable degree of higher precision than that afforded by binarization. For example, instead of two subpopulation, one might chose to segregate intensities into eight subpopulations or 16 subpopulations. Inherent in this representation is the information represented in the form of weights in the binary representation discussed herein above. Each digitized normalized intensity in fact represents a measure of the coaffinity of a particular probe-target interaction (see U.S. application Ser. No. 10/204,799 "Multianalyte Molecular Analysis"; WO 01/98765). Experimental digitized reaction patterns, and reference digitized patterns are compared by means of computing cross-correlations using standard methods.

Multi-user Remote Access, Application Serving—Use of a program also allows the establishing of a network to permit remote analysis, redaction and reporting of results of allele assignment. For example, a database which forms part of the AAA software environment, may be accessed via a secure network connection. The AAA program also supports an application service mode permitting interactive editing from a location other than the location of the experimental laboratory.

Preferred Embodiment of Multiplexed Analysis: Random Encoded Array Detection—In one format of multiplexed analysis, detection probes are displayed on encoded microparticles ("beads"). Labels are associated with the targets. The encoded beads bound to the probes in the array are preferably fluorescent, and can be distinguished using filters which permit discrimination among different hues. Preferably, sets of encoded beads are arranged in the form of a random planar array on a planar substrate, thereby permitting examination and analysis by microscopy. Intensity of target labels are monitored to indicate the quantity of target bound per bead. This assay format is explained in further detail in International Publication No. WO 01/98765 entitled: "Multianalyte molecular analysis," incorporated by reference. Several methods of producing optical signatures are available, for example by capture of labeled targets or by target-mediated probe elongation (eMAP), the latter preferably performed by using immobilized allele-specific oligonucleotides capable of priming a polymerase-catalyzed elongation reaction. (see, e.g., International Publication No. WO 03/034029). One or more suitable targets are produced, for example, by reverse transcription of RNA and/or amplification of genomic DNA, optionally followed by additional steps such as fragmentation (see U.S. Provisional Application 60/515,413), denaturation or strand selection (U.S. application Ser. No. 10/847,046).

Subsequent to recording of a decoding image of the array of beads, the array is exposed to the targets under conditions permitting capture to particle-displayed probes. After a suitable reaction time, the array of encoded particles is washed to remove remaining free and weakly annealed targets. An assay image of the array is then taken to record the optical signal of the probe-target complexes of the array (or to record the signal from elongated probes, in the event capture-mediated elongation is the assay format being used). Because each type of particle is uniquely associated with a sequence-specific probe, the decoding step permits the identification of annealed target molecules determined from fluorescence of each particular type of particle.

A fluorescence microscope is used for decoding. The fluorescence filter sets in the decoder are designed to distinguish fluorescence produced by encoding dyes used to stain particles, whereas other filter sets are designed to distinguish assay signals produced by the dyes associated with the targets. A CCD camera may be incorporated into the system for recording of decoding and assay images. The assay image is analyzed to determine the identity of each of the captured targets by correlating the spatial distribution of signals in the assay image with the spatial distribution of the corresponding encoded particles in the array.

In this format of multiplexed analysis, there is a limitation on the number of probe types, in that the total number of bead types in the array is limited by the encoding method used (e.g., the number of distinguishable colors available) and by the limits of the instrumentation used for interpretation, e.g., the size of the field in the microscope used to read the array. One must also consider, in selecting probes, that certain probes hybridize more efficiently to their target than others, under the same conditions. Hybridization efficiency can be affected by a number of factors including interference among neighboring probes, probe length and probe sequence, and, significantly, the temperature at which annealing is conducted. A low hybridization efficiency may result in a false negative signal. Accordingly, an assay design should attempt to correct for such low efficiency probe/target annealing.

After an actual assay has been performed, the Array Imaging System (as described in U.S. application Ser. No. 10/714, 203, incorporated by reference) can be used to generate an assay image, which can be used to determine the intensity of hybridization signals from various beads (probes). The assay image can then be applied by a system for automatic allele assignment, as described herein.

EXAMPLES

I. Allele Assignment—By way of illustration (see also the "screen shot illustration" in FIG. 3), AAA, using the core probe set of probes, lists two suggested group allele assignments, namely A*03+A*29 and A*29+A*74. The two groups are ranked in the order of the weights of flipped probes. The lower the weight, the higher the rank of the groups. If the core probe set produces degenerate suggested assignments, as in this case, the analysis is automatically repeated using the expanded probe set. This second pass produces a suggested assignment of A*03+A*29 which would require the flipping of HA120+, indicating that HA120 may represent a false positive. The reaction pattern and hit table (for HLA-A alleles) also are displayed in the screen shot. In the reaction pattern, 8 indicates the probe is positive, 1 negative and 0 means the probe is not used.

In the manual redaction mode, the user can edit the initial allele assignments by checking the known references for the alleles identified in the core and expanded sets, and then conforming the bit strings to those expected from the known alleles. Verifying the experimental results against the known alleles in this manner provides a validation of the assay results, and a means to edit the bit string. User picks A*03011 and A*2901101 as assignment, HA120 as flip probe in manual redaction mode in FIG. 4.

Example II

Allele Frequency Statistics 1155 samples were screened using in an HLA-A panel, and the sample intensity patterns were analyzed using the AAA program to obtain two-digit allele group

| Allele # | Count | Frequency |
|---|---|---|
| 01 | 332 | 0.144 |
| 02 | 448 | 0.194 |
| 03 | 251 | 0.109 |
| 11 | 139 | 0.060 |
| 23 | 86 | 0.037 |
| 24 | 260 | 0.113 |
| 25 | 30 | 0.013 |
| 26 | 203 | 0.088 |
| 29 | 87 | 0.038 |
| 30 | 105 | 0.045 |
| 31 | 46 | 0.020 |
| 32 | 66 | 0.029 |
| 33 | 86 | 0.037 |
| 34 | 6 | 0.003 |
| 36 | 4 | 0.002 |
| 43 | 0 | 0.000 |
| 66 | 25 | 0.011 |
| 68 | 100 | 0.043 |

-continued

| Allele # | Count | Frequency |
|---|---|---|
| 69 | 28 | 0.012 |
| 74 | 5 | 0.002 |
| 80 | 3 | 0.001 |
|  | 2310 |  | assignments. The count and relative frequency of occurrence of group calls calculated by the AAA program are shown in Table 1, immediately below.

The bar-graph for the following distribution is shown in FIG. 1. It is evident the alleles 01, 02 and 03 are much more abundant in this population whereas alleles 36, 43 and 80 are comparatively rare.

Example III

Assignment Summary Information Screen Shot

The screen shot in FIG. 3 illustrates the assignment summary information for panel 0320443. It includes panel name, sample name, sample position, allele assignment, flip probes, warning message and comments. The allele assignment lists the allele level assignment by computer algorithm. The flips and warning messages will be displayed according to computer assignment as well. If there is manual redaction, the allele assignment will be by the manual redactor's choice pick. See FIG. 4 for an illustration of manual redaction. The comment and flips input during any manual redaction are also displayed. The flip probes will be inserted to a (manual) string in the end, which indicates it is generated by manual redaction.

The software lists the first two digit of the allele assignment and the following digits, if applicable. For instance, A*24 (020101) indicates the two digit call is A*24. The summary information window displays all vital information in one window, which makes it easy to examine and navigate through different samples.

Example IV

Three-Letter Alphabet: Blood Group Antigen Molecular Typing

In a set of approximately 500 clinical samples and controls, several allele combinations were identified by an eMAP assay design, designed to probe minor blood group antigens including Duffy (FYA/FYB), GATA, Landsteiner-Weiner (LWA/LWB), Colton (CoA/CoB), Scianna (SC1/SC2), Diego (DIA/DIB) and Dombrock (DoA/DoB), the latter comprising three mutations. See Table 2 below.

TABLE 2

Observed Allele Combinations of Minor Human Blood Group Antigens

| Sample ID | FYA/FYB | GATA | LWA/LWB | COA/COB | SC1/SC2 | DIB/DIA | DO-793 | DO-624 | DO-378 |
|---|---|---|---|---|---|---|---|---|---|
| N21 BAS | −1 | −1 | 1 | 1 | 1 | 1 | −1 | −1 | −1 |
| N40 BAS | −1 | 0 | 1 | 1 | 1 | 1 | −1 | −1 | −1 |
| M17 | 0 | 0 | 1 | 1 | 1 | 1 | −1 | −1 | −1 |
| A10 | −1 | 1 | 1 | 1 | 1 | 1 | −1 | −1 | −1 |
| A4 | 0 | 1 | 1 | 1 | 1 | 1 | −1 | −1 | −1 |
| A1 | 1 | 1 | 1 | 1 | 1 | 1 | −1 | −1 | −1 |
| N39 BAS | −1 | −1 | 1 | 1 | 1 | 1 | −1 | −1 | 0 |

TABLE 2-continued

Observed Allele Combinations of Minor Human Blood Group Antigens

| Sample ID | FYA/FYB | GATA | LWA/LWB | COA/COB | SC1/SC2 | DIB/DIA | DO-793 | DO-624 | DO-378 |
|---|---|---|---|---|---|---|---|---|---|
| N71 | −1 | 0 | 1 | 1 | 1 | 1 | −1 | −1 | 0 |
| N62-BAS | 0 | 0 | 1 | 1 | 1 | 1 | −1 | −1 | 0 |
| N66-BAS | −1 | −1 | 1 | 1 | 1 | 1 | −1 | −1 | 1 |
| 1 | −1 | 0 | 1 | 1 | 1 | 1 | −1 | −1 | 1 |
| N72 | −1 | 1 | 1 | 1 | 1 | 1 | −1 | −1 | 1 |
| M12 | −1 | 1 | 1 | 1 | 1 | 1 | −1 | −1 | 1 |
| 16 | −1 | −1 | 1 | 1 | 1 | 1 | 0 | 0 | −1 |
| 34 | −1 | 0 | 1 | 1 | 1 | 1 | 0 | 0 | −1 |
| A21 | −1 | 1 | 1 | 1 | 1 | 1 | 0 | 0 | −1 |
| N34 BAS | 0 | 0 | 1 | 1 | 1 | 1 | 0 | 0 | −1 |
| A28 | 0 | 1 | 1 | 1 | 1 | 1 | 0 | 0 | −1 |
| A14 | 1 | 1 | 1 | 1 | 1 | 1 | 0 | 0 | −1 |
| N70 | −1 | −1 | 1 | 1 | 1 | 1 | 0 | 0 | 0 |
| A6 | 0 | 1 | 1 | 1 | 1 | 1 | 0 | 0 | 0 |
| A7 | 1 | 1 | 1 | 1 | 1 | 1 | 0 | 0 | 0 |
| N78-BAS | −1 | −1 | 1 | 1 | 1 | 1 | 0 | 0 | 1 |
| 2 | −1 | 1 | 1 | 1 | 1 | 1 | 1 | 1 | 0 |
| M23 | 0 | 1 | 1 | 1 | 1 | 1 | 1 | 1 | 0 |
| U79 | 1 | 1 | 1 | 1 | 1 | 1 | 1 | 1 | 0 |
| N35 BAS | −1 | −1 | 1 | 1 | 1 | 1 | 1 | 1 | 1 |
| N51 | −1 | 0 | 1 | 1 | 1 | 1 | 1 | 1 | 1 |
| A9 | −1 | 1 | 1 | 1 | 1 | 1 | 1 | 1 | 1 |
| 26 | −1 | 1 | 1 | 1 | 0 | 1 | 1 | 1 | 1 |
| 62 | −1 | 1 | 1 | 1 | 1 | 1 | 1 | 1 | 1 |
| N51-BAS | 0 | 0 | 1 | 1 | 1 | 1 | 1 | 1 | 1 |
| A25 | 0 | 1 | 1 | 1 | 1 | 1 | 1 | 1 | 1 |
| N7 BAS | 1 | 1 | 1 | 1 | 1 | 1 | 1 | 1 | 1 |

Example V

Establishing Relationships to Diseases and Conditions

Allele assignments determined by the foregoing methods can also be used to establish risk or presence of diseases or conditions. It is well known that certain immune disorders are associated with the HLA locus. The associated alleles can be typed, if known, and if unknown, the methods described herein can be used to establish an allele database to indicate risk or presence of diseases or conditions. The database can be continually updated based on monitoring of patients whose samples were used in the database; i.e., as some develop the disease, their alleles can be analyzed to determine commonality of those with a particular disease or condition.

It should be understood that the terms, expressions and examples herein are exemplary and not limiting, and that the invention is defined only in the claims which follow, and includes all equivalents of the subject matter of the claims. The method steps in the claims are not necessarily in order, and unless specified in the claim, may be carried out in any order, including that specified in the claims.

What is claimed is:

1. A method for allele assignments where assignments are made on the basis of subjecting a sample including target nucleic acid to a hybridization assay or capture-mediated elongation assay, or both, and where several polymorphic markers, present on alleles in the target nucleic acid are analyzed, the method comprising:
    determining the assay signal intensity pattern generated by probe-target interactions where each said intensity corresponds to the number of corresponding hybridization or elongation events, as applicable;
    binarizing said interaction pattern to generate a reaction pattern by designating as positive those signal intensities exceeding a pre-determined threshold and designating as negative those signal intensities not exceeding a pre-determined threshold;
    making allele assignments based on comparing and matching said reaction pattern with a similar reference reaction pattern representing combinations of two or more reference alleles, as listed in a reference collection of alleles for the target nucleic acid under consideration;
    designating as new alleles, those having reaction patterns which differ from reference reaction patterns representing combinations of two or more reference alleles by a pre-determined minimal dissimilarity; and
    displaying the allele assignments in a user readable form.

2. The method of claim 1 wherein said reaction pattern is edited based on comparison with the reference reaction pattern.

3. The method of claim 1 further including the step of making initial allele assignments which are then confirmed or changed following said comparing and matching steps.

4. The method of claim 1 wherein the similar reference reaction pattern selected for comparison is the most similar reference reaction pattern.

5. The method of claim 1 wherein the capture-mediated elongation assay generates a positive assay signal when elongation takes place.

6. A method for allele assignments where assignments are made on the basis of subjecting a sample including target nucleic acid to a hybridization assay or capture-mediated elongation assay, or both, and where several polymorphic markers, present on alleles in the target nucleic acid are analyzed, the method comprising:
    determining the assay signal intensity pattern generated by probe-target interactions where each said intensity corresponds to the number of corresponding hybridization or elongation events, as applicable;
    binarizing said assay signal intensity pattern to generate a reaction pattern by designating as positive those signal intensities exceeding a pre-determined threshold and designating as negative those signal intensities not exceeding a pre-determined threshold;

comparing said reaction pattern with a reference reaction pattern representing combinations of two or more reference alleles, as listed in a reference collection of alleles for the target nucleic acid under consideration;

flipping at least one result from a reaction in said reaction pattern (i.e., positive to negative or vice-versa) to conform said reaction pattern with a reference reaction pattern; and displaying the allele assignments in a user readable form.

7. The method of claim 6 wherein the pre-determined threshold for at least one reaction is changed so as to minimize the number of reversals required to conform said reaction pattern with the reference reaction pattern.

8. The method of claim 6, further including the step of subtracting from each signal intensity, I, the negative control signal, $I_{NC}$, and dividing the result by the corrected positive control signal, $I_{PC}$, to obtain a normalized intensity (ratio):

$$r=(I-I_{NC})/(I_{PC}-I_{NC}).$$

9. The method of claim 6, further including the step of selecting said pre-determined threshold so as to maximize the similarity between said reaction pattern and a reference reaction pattern.

10. The method of claim 6 further including the step of making initial allele assignments based on comparing said reaction pattern to a reference reaction pattern but then changing the initial allele assignments following conforming said reaction pattern with a reference reaction pattern.

11. The method of claim 6, further including the step of selecting said pre-determined threshold so as to maximize the similarity between said reaction pattern and a reference reaction pattern.

12. A method of identifying new alleles where allele assignments are made on the basis of subjecting a sample including target nucleic acid to a hybridization assay or capture-mediated elongation assay, or both, and where several polymorphic markers, present on alleles in the target nucleic acid are analyzed, the method comprising:

determining the assay signal intensity pattern generated by probe-target interactions where each said intensity corresponds to the number of corresponding hybridization or elongation events, as applicable;

binarizing said interaction pattern to generate a reaction pattern by designating as positive those signal intensities exceeding a pre-determined threshold and designating as negative those signal intensities not exceeding a pre-determined threshold;

comparing said reaction pattern with a reference reaction pattern representing combinations of two or more reference alleles, as listed in a reference collection of alleles for the target nucleic acid under consideration;

designating as new alleles, those having reaction patterns which differ from reference reaction patterns representing combinations of two or more reference alleles by a pre-determined minimal dissimilarity; and displaying the allele assignment in a user readable form.

13. The method of claim 12 wherein said minimal dissimilarity is a minimal Hamming distance.

14. The method of claim 12 wherein the minimal dissimilarity is weighted, so that certain differences between said reaction pattern and said reference reaction pattern generate a greater dissimilarity than others.

15. The method of claim 12, further including the step of subtracting from each signal intensity, I, a negative control signal, $I_{NC}$, and dividing the result by a corrected positive control signal, $I_{PC}$, to obtain a normalized intensity (ratio):

$$r=(I-I_{NC})/(I_{PC}-I_{NC}).$$

16. A method of assigning alleles where allele assignments are made on the basis of subjecting a sample including target nucleic acid to a hybridization assay or capture-mediated elongation assay, or both, and where several polymorphic markers, present on alleles in the target nucleic acid are analyzed, the method comprising:

determining the assay signal intensity pattern generated by probe-target interactions where each said intensity corresponds to the number of corresponding hybridization or elongation events, as applicable;

binarizing said interaction pattern to generate a reaction pattern by designating as positive those signal intensities exceeding a pre-determined threshold and designating as negative those signal intensities not exceeding a pre-determined threshold;

comparing said reaction pattern with a reference reaction pattern representing combinations of two or more reference alleles, as listed in a reference collection of alleles for the target nucleic acid under consideration;

assigning a reaction pattern as either a group of alleles or assigning it as an individual allele, based on comparing said reaction pattern with a reference reaction pattern from either a group of alleles or from an individual allele, as applicable, and then determining the most appropriate assignment;

designating as new alleles, those having reaction patterns which differ from reference reaction patterns representing combinations of two or more reference alleles by a pre-determined minimal dissimilarity; and displaying the allele assignment in a user readable form.

17. The method of claim 16 wherein the resolution of the actual reaction pattern is sufficient to allow assignment to an allele group, but not as an individual allele.

18. The method of claim 16, further including the step of subtracting from each signal intensity, I, a negative control signal, $I_{NC}$, and dividing the result by a corrected positive control signal, $I_{PC}$, to obtain a normalized intensity (ratio):

$$r=(I-I_{NC})/(I_{PC}-I_{NC}).$$

\* \* \* \* \*